United States Patent [19]

Clauson-Kaas et al.

[11] 4,192,946
[45] Mar. 11, 1980

[54] PROCESS FOR PRODUCING 3-HYDROXY-5-HALOPYRIDINES

[75] Inventors: Niels Clauson-Kaas, Farum, Denmark; Gunter Mattern, Liestal; Walter Traber, Reinach, both of Switzerland

[73] Assignee: Ciba-Geigy Corporation, Ardsley, N.Y.

[21] Appl. No.: 920,425

[22] Filed: Jun. 29, 1978

[51] Int. Cl.$^2$ .......................................... C07D 213/02
[52] U.S. Cl. ................................................... 546/249
[58] Field of Search ....................... 546/250, 249, 303

[56] References Cited

U.S. PATENT DOCUMENTS

| 3,808,218 | 4/1974 | Kristinsen | 546/23 |
| 3,850,943 | 11/1974 | Bowden et al. | 546/303 |

FOREIGN PATENT DOCUMENTS

| 1134378 | 2/1963 | Fed. Rep. of Germany | 546/303 |
| 2245363 | 9/1971 | Fed. Rep. of Germany | 546/303 |
| 862581 | 3/1961 | United Kingdom | 546/23 |

OTHER PUBLICATIONS

Recueil 69, 1281 (1950).
Recueil 70, 185 (1951).
Chem. Abstracts, vol. 58, 1438f.

*Primary Examiner*—Alan L. Rotman
*Assistant Examiner*—Robert C. Whittenbaugh
*Attorney, Agent, or Firm*—Harry Falber

[57] ABSTRACT

A process for the production of 3-hydroxy-5-chloropyridine and 3-hydroxy-5-bromopyridine is disclosed which process comprises reacting 2-furfurylamine in aqueous mineral-acid solution at $-20°$ to $+5°$ C. with chlorine or bromine, neutralizing the hydrohalic acid formed, heating the reaction mixture at reflux temperature, and isolating the formed 3-hydroxy-5-halopyridine. The 3-hydroxy-5-halopyridines obtained are intermediates for the production of insecticides.

9 Claims, No Drawings

PROCESS FOR PRODUCING 3-HYDROXY-5-HALOPYRIDINES

The present invention relates to a new process for producing 3-hydroxy-5-halopyridines of the formula I

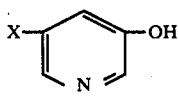

wherein
X represents chlorine or bromine.

The 3-hydroxy-5-halopyridines of the formula I are valuable intermediates for producing pesticidal compositions. They can be converted for example by nitration in the 2-position and subsequent reduction into the corresponding 2-amino-3-hydroxy-5-halopyridines, which yield on further reaction with phosgene the corresponding 6-chloro-oxazolo[4,5-b]pyridin-2(3H)-ones, which can firstly be converted with formaldehyde and thionyl chloride into the corresponding 3-chloromethyl-6-halo-oxazolo[4,5-b]pyridin-2(3H)-ones, from which can then be produced, by reaction with alkali dialkyl phosphates or ammonium dialkyl phosphates or alkali dialkyl thiophosphates or ammonium dialkyl thiophosphates, phosphoric esters of the formula

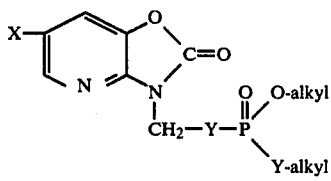

wherein Y represents oxygen or sulphur, and X has the meaning given under the formula I. Phosphoric esters of this type have an excellent insecticidal action (see U.S. Pat. No. 3,808,218).

It is known that 3-hydroxy-5-halopyridines of the formula I can be produced by firstly converting a 3,5-dihalopyridine with sodium ethylate into a 3-ethoxy-5-halopyridine, and subsequently hydrolyzing this to give the corresponding 3-hydroxy-5-halopyridine (H. J. den Hertog et al., Recueil des Travaux Chimiques des Pays-Bas, 69, 1281 (1950), ibid. 70, 185 (1951).

Further, 5-chloro-3-hydroxypyridine can be prepared from 5-chloronicotinamide (Rocz. Chem. 34, 905–915 (1960)). According to this method 5-chloronicotinamide is converted by Hofmann-degradation into 3-amino-5-chloropyridine which is subsequently either diazotized and hydrolysed or nitrated to 5-chloro-3-nitraminopyridine and hydrolysed with sulfuric acid, to obtain 5-chloro-3-hydroxypyridine.

A further known process for producing 3-hydroxy-5-halopyridines comprises firstly nitrating 3-hydroxypyridine in the 5-position, reducing the product obtained to the corresponding 5-amino compound, diazotizing this, and then reacting the resulting product with a copper(I) halide to obtain a 3-hydroxy-5-halopyridine (see German Offenlegungsschrift No. 2,245,363). The 3-hydroxypyridine used as starting material in this process can be produced by the process described in the German Pat. No. 1,134,378, or by the process described in the British Pat. No. 862,581.

The aforementioned known processes for producing 3-hydroxy-5-halopyridines of the formula I are unfavourable not only because they are complicated but also because only moderate yields of 3-hydroxy-5-halopyridines are obtained. These known processes are therefore not suitable for producing 3-hydroxy-5-halopyridines of the formula I commercially.

It is the object of the present invention to provide a process of producing 3-hydroxy-5-halopyridines of the formula I, by means of which process it is possible to obtain the 3-hydroxy-5-halopyridines of the formula I in a simple manner, in good yields, and with the use of cheap, easily available starting materials.

The process according to the invention comprises reacting 2-furfurylamine in an aqueous mineral-acid solution at −20° to +5° C. with halogen, neutralizing the formed hydrohalic acid, heating the reaction mixture at reflux temperature, cooling it and then isolating the formed 3-hydroxy-5-halopyridine of the formula I.

Suitable mineral acids in the presence of which the reaction of 2-furfurylamine with halogen is carried out are sulphuric acid, phosphoric acid, hydrochloric acid and hydrobromic acid. The acids preferably used are hydrochloric acid and hydrobromic acid; for the reaction with chlorine only hydrogen chloride can be used. The mineral acid is employed in an amount sufficient to dissolve the 2-furfurylamine in the aqueous reaction medium. For this purpose there is required in practice 0.60 to 1 equivalent of mineral acid per mol of 2-furfurylamine. There is preferably used however 0.8 to 0.9 equivalent of mineral acid per mol of 2-furfurlyamine.

The halogen used is chlorine or bromine in accordance with the definition given for X under the formula I. For the reaction of furfurylamine to a 3-hydroxy-5-halopyridine of the formula I, 2 mols of halogen are required. For carrying out the process according to the invention, 1.90 to 2.25 mols of halogen per mol of furfuryl can be used. It is however advantageous to use the halogen in an excess of 0.01 to 0.20 mol per mol of 2-furfurylamine.

The addition of halogen and its reaction with 2-furfurylamine are performed in the temperature range of between −20° and +5° C. Preferably, the addition and the reaction of the halogen with furfurylamine are carried out at temperatures of −15° to −5° C. The addition of halogen should not be made too rapidly. As a rule, the addition requires between 5 and 10 hours. After completed addition of halogen, it is advantageous to allow the reaction mixture to react for some time in the same temperature range in which the addition of halogen has been made. The times necessary for this are between 4 and 20 hours, depending on the reaction temperature. A part of the acid present in the reaction mixture is subsequently neutralised. This neutralisation extends essentially to the hydrohalic acid formed during the reaction of furfurylamine with halogen. The neutralisation is effected by addition of the concentrated aqueous solution of a base, preferably of an alkali metal hydroxide, e.g. sodium hydroxide or potassium hydroxide.

The partially neutralised reaction mixture, which has a pH value of about 1, is then heated to reflux temperature and held there for 5 to 15 minutes. The reaction mixture is subsequently cooled, and neutralised by addition of an aqueous alkali metal hydroxide solution to pH 5 to 6, in the course of which the formed 3-hydroxy-5-halopyridine of the formula I is precipitated. It is separated by filtration, dried, and optionally purified by recrystallisation.

A preferred embodiment of the process according to the invention comprises starting with an aqueous solution of furfurylamine containing 0.80 to 0.90 mol of hydrogen halide per mol of furfurylamine, adding in the course of 7 hours at −15° to −5° C. 2.01 to 2.20 mols of halogen, stirring for 6 to 8 hours at −15° to −5° C., neutralising the reaction mixture by the addition of concentrated aqueous alkali metal hydroxide solution to pH 1, subsequently heating at reflux temperature for 5 to 10 minutes, cooling to 60° to 80° C., neutralising the mixture to pH 5.3, and separating the formed 3-hydroxy-5-halopyridine of the formula I by filtration.

The process according to the invention renders possible, starting with furfurylamine, the production of 3-hydroxy-5-halopyridines of the formula I, in a single-vessel process, in yields of 75 to 80% of theory. Compared with known processes, the process according to the invention is considerably more simple to perform, gives substantially higher yields, and is far more suitable than the known processes for the commercial production of 3-hydroxy-5-halopyridines of the formula I. The process according to the invention is suitable in particular for producing 3-hydroxy-5-chloropyridine.

The 2-furfurylamine required as starting material can be produced in a simple manner by reductive amination of furfurol.

The process according to the invention is further illustrated by the Examples which follow.

EXAMPLE 1

38.8 parts (0.4 mol) of 2-furfurylamine are introduced at 10° C. into a mixture of 34 parts of concentrated hydrochloric acid and 120 parts of water. Into the resulting orange-coloured solution are fed at −15° to −5° C., in the course of 7 hours, 61 parts (0.86 mol) of chlorine. The light-yellow solution is subsequently stirred under nitrogen for 17 hours at −20° C., and during this time a light stream of nitrogen is passed through the solution to remove the excess chlorine. There are then added at −10° to −5° C. during 75 minutes 90 parts of 40% aqueous sodium hydroxide solution, and the resulting pH value is 1. The brown suspension obtained is heated during 5 minutes at reflux temperature; the temperature is then lowered to about 80° C., and the pH value of the mixture is adjusted to 5.3 by the addition of 40% aqueous sodium hydroxide solution (about 70 parts). The reaction mixture is cooled with stirring to room temperature, and the crude 3-hydroxy-5-chloropyridine which has precipitated is separated by filtration, washed with water and dried at 100° C. for 1 hour.

41 parts of the product obtained in this manner are taken up in 150 parts of boiling methanol, and separated at 60° C. from the undissolved residue. The residue left after concentrating the filtrate by evaporation is dried at 80° C. for 2 hours. There are obtained by this procedure 38.7 parts (74.7% of theory) of 3-hydroxy-5-chloropyridine having a melting point of 156° to 159° C.

EXAMPLE 2

11 ml (34.5 g; 0.216 mol) of bromine is added dropwise at −10° C., in the course of 6½ hours, to a solution of 9.7 g (0.1 mol) of 2-furfurylamine in 43.4 g of 11.5% hydrobromic acid (5.0 g of HBr; 0.062 mol). The solution obtained is subsequently stirred under nitrogen for 16 hours at −20° C. A stream of nitrogen is passed through the resulting orange suspension for 1 hour at −10° C. The red solution thus obtained is brought to pH 1 by addition of concentrated aqueous sodium hydroxide solution, resulting in a brown suspension being formed. This is heated during 50 minutes to reflux temperature and held there for 5 minutes. The dark solution formed is cooled to 80° C., and neutralised to pH 5.3 by the addition of concentrated aqueous sodium hydroxide solution. The crude product which has precipitated is separated by filtration, and dried at 100° C. in vacuo. The crude product (9.9 g) is subsequently taken up at boiling temperature in 40 ml of methanol, and filtered hot. Concentration of the filtrate by evaporation yields 8.1 g of brown product, from which is obtained, by recrystallisation from toluene, 3.5 g of 3-hydroxy-5-bromopyridine having a melting point of 162° to 164° C.

EXAMPLE 3

38.8 ml (0.4 mol) of 2-furfurylamine is introduced at 10° C. into a mixture of 42 ml of 98% sulphuric acid (0.78 mol) and 120 ml of water. Into the solution obtained is then passed at −15° C., in the course of 6½ hours, 61.0 g (0.86 mol) of chlorine. The very dark green solution is allowed to stand under nitrogen at −20° C. overnight. The temperature is then raised to −10° C., and nitrogen is fed for 1 hour through the reaction mixture. The pH value is subsequently adjusted at −5° to 10° C. to 1 by the addition of 240 ml of 40% sodium hydroxide solution. The resulting solution is then heated within 45 minutes to reflux temperature, and held there for 5 minutes. After the solution has cooled to 80° C., the pH value of the brown suspension is brought to 5.3 by the addition of 40% sodium hydroxide solution. Filtration at room temperature is subsequently performed, and the filter residue is washed with a small amount of ice-water. The brown crude product is dried at 100° C. for one hour, and then boiled for 15 minutes in 150 ml of methanol, and afterwards filtered hot. The filtrate is concentrated to dryness in vacuo, and the residue is recrystallised from 150 ml of isobutyl methyl ketone to thus yield pure 3-hydroxy-5-chloropyridine having a melting point of 157° to 159° C.

EXAMPLE 4

A solution of 38.8 ml (0.4 mol) of 2-furfurylamine in a mixture of 42.5 ml of 99% phosphoric acid (0.78 mol) and 120 ml of water is chlorinated and worked up in the way described in Example 3. There is obtained 12.6 g (24.5% of theory) of 3-hydroxy-5-chloropyridine having a melting point of 157° to 159° C.

We claim:

1. Process for producing 3-hydroxy-5-halopyridines of the formula

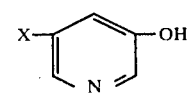

wherein

X represents chlorine or bromine, which process comprises reacting 2-furfurylamine in aqueous mineral-acid solution at −20° to +5° C. with 1.90 to 2.25 mols of halogen per mole of 2-furfurylamine, neutralising the hydrohalic acid formed, heating the reaction mixture at reflux temperature, cooling it, and isolating the formed 3-hydroxy-5-halopyridine of the formula I.

2. Process according to claim 1, wherein the reaction of 2-furfurylamine with halogen is performed in the presence of sulphuric acid, phosphoric acid, hydrochloric acid or hydrobromic acid.

3. Process according to claim 1, wherein the reaction of 2-furfurylamine with halogen is performed in the presence of hydrochloric acid or hydrobromic acid, with only hydrochloric acid being applicable for the reaction of 2-furfurylamine with chlorine.

4. Process according to claim 1, wherein there is used a mineral-acid solution of 2-furfurylamine, which solution contains 0.6 to 1 equivalent of mineral acid per mole of 2-furfurylamine.

5. Process according to claim 1, wherein there is used a mineral-acid solution of 2-furfurylamine, which solution contains 0.8 to 0.9 equivalent of mineral acid.

6. Process according to claim 1, wherein 2.01 to 2.20 mols of halogen are used per mol of 2-furfurylamine.

7. Process according to claim 1, wherein the reaction of 2-furfurylamine with halogen is performed at a temperature of −15° to −5° C.

8. Process according to claim 1, wherein the reaction mixture is neutralised by the addition of an aqueous alkali metal hydroxide solution to pH 5 to 6 in order to separate the formed 3-hydroxy-5-halopyridine of the formula I.

9. Process according to claim 1, which process comprises adding to an aqueous solution of 2-furfurylamine containing 0.80 to 0.9 mol of hydrogen halide per mol of 2-furfurylamine, in the course of 7 hours at −15° to −5° C., 2.01 to 2.20 mols of halogen, stirring for 6 to 8 hours at −15° to −5° C., neutralising the reaction mixture to pH 1 by the addition of concentrated aqueous alkali metal hydroxide solution, heating the mixture for 5 to 10 minutes at reflux temperature, cooling it to 60° to 80° C., subsequently neutralising it to pH 5.3, and separating the formed 3-hydroxy-5-halopyridine of the formula I.

* * * * *